(12) United States Patent
Heidemann et al.

(10) Patent No.: US 6,953,692 B2
(45) Date of Patent: Oct. 11, 2005

(54) DEVICE AND METHOD FOR SEED-TRAIN EXPANSION OF MAMMALIAN CELLS

(75) Inventors: Rudiger Heidemann, Emeryville, CA (US); Mokhtar Mered, Orinda, CA (US); James D. Michaels, Oakland, CA (US); Konstantin Konstantinov, Walnut Creek, CA (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 6 days.

(21) Appl. No.: 10/029,779

(22) Filed: Dec. 18, 2001

(65) Prior Publication Data

US 2003/0113915 A1 Jun. 19, 2003

(51) Int. Cl.[7] ................................................. C12N 5/00
(52) U.S. Cl. ................. 435/383; 435/303.3; 435/305.1; 435/305.2; 435/325; 435/352; 435/358; 435/289.1
(58) Field of Search ...................... 435/383, 358, 435/303.3, 352, 325, 289.1, 305.1, 305.2

(56) References Cited

U.S. PATENT DOCUMENTS 4,049,494 A * 9/1977 Tomei ........................ 435/239
4,978,616 A * 12/1990 Dean et al. ................. 435/70.3

OTHER PUBLICATIONS

Whitaker et al., Journal of the American Chemical Society, pp. 28–43, 1998.*

* cited by examiner

Primary Examiner—Leon B. Lankford, Jr.
(74) Attorney, Agent, or Firm—John W. Mahoney

(57) ABSTRACT

A device and method for seed-train expansion of a source of mammalian cells and their use in production of proteins expressed by the cells comprising the use of a dedicated inoculation bioreactor for expanding the cells prior to the transfer to a production bioreactor is disclosed.

The novel inoculation bioreactor is designed to facilitate an improved method of mammalian cell seed-train expansion, and is distinguished by the presence of an "inoculation well" which communicates with the interior of the bioreactor and which facilitates the growth of mammalian cells for commercial seed-train expansion.

The method comprises adding the cryopreserved cells to media within the inoculation well of the inoculation bioreactor, enabling the cells to grow to a predetermined concentration within the inoculation well by monitoring and adjusting the condition of the media and environment, and thereafter incrementally increasing the volume of the media within the reactor so that optimal cell growth is maintained.

6 Claims, 9 Drawing Sheets

Inoculation well

Inoculation well

DEVICE AND METHOD FOR SEED-TRAIN EXPANSION OF MAMMALIAN CELLS

RELATED APPLICATIONS

This Application claims priority of application Ser. No. 09/746,972 filed on Dec. 20, 2000, which was converted to a Provisional Application under 37 C.F.R. §1.53(c)(2) on Dec. 14, 2001, which is herein incorporated by reference.

BACKGROUND OF THE INVENTION

1. Field

This invention relates to manufacturing scale mammalian cell culture technology and specifically to a new seed-train expansion method for mammalian cells. Cryopreserved cells are used to inoculate directly into a newly designed bioreactor, which serves as a seed source for production scale.

2. Background

The start of a new cell seed-train expansion for a production campaign for the expression of a mammalian cell culture system is a critical process step. Operational inconsistencies and errors often compromise the process, leading to significant delays and inoculum variability. In typical production protocols, a new seed train expansion begins from a 1–2 mL cryovial (master working cell bank, MWCB). The cell concentration of this container is usually in the range of 5–10 million cells/mL. The cells are thawed, washed to remove the cryoprotectant and then first cultured (seeded) in small tissue culture flasks. It is standard practice with mammalian cell cultures to use inoculation densities of 0.5 to $1 \times 10^6$ cells/mL. Seeding cells at lower cell concentrations after cryopreservation may result in an extended lag phase prior to entering the growth phase, poor cell performance or even cell death. This is especially accentuated in the serum-free or even protein-free cell culture media that has become the modus operandi for current cell culture manufacturing.

The cells are sub-cultivated according to their specific growth rate (cell density), and are usually split into multiple cell culture flasks every 2–3 days. Once enough biomass is produced, the cells are expanded into larger cultivation bottles such as roller bottles, shake or spinner flasks. After enough cell mass is accumulated, a bioreactor, which becomes the seed culture for the production-scale vessel, is inoculated. This described seed-train expansion is general practice for several mammalian cell lines and is widely used in commercial production and academia. An overview of a commercial seed train expansion using T-flasks and spinner flasks is also given by Whitaker et al., *Journal of the American Chemical Society*, pages 28–43, 1998.

Typical scale-up protocols which take about four to six weeks to complete under optimal conditions are labor intensive and are susceptible to contamination and variability. The small scale conditions are not well defined—usually there is no set-point for pH and DO during the T-flask, roller bottle or shaker flask period, which may lead to more variability throughout the process and might compromise the quality of the inoculum and the product.

SUMMARY OF THE INVENTION

We have developed a novel bioreactor and method for the seed-train expansion of mammalian cells. This technology eliminates the use of tissue culture-flasks, roller bottles or shake flasks.

Our novel inoculation bioreactor is designed to facilitate an improved method of mammalian cell seed-train expansion, and is distinguished by the presence of an "inoculation well" which communicates with the interior of the bioreactor and which facilitates the growth of mammalian cells for commercial seed-train expansion.

Our method for seed-train expansion of cryopreserved cells comprises the use of a dedicated inoculation bioreactor having an inoculation well for expanding the cells prior to their transfer to a production bioreactor. More specifically, our method comprises adding the cryopreserved cells to media within the inoculation well of the inoculation bioreactor, enabling the cells to grow to a predetermined concentration within the inoculation well by monitoring and adjusting the condition of the media and environment, and thereafter incrementally increasing the volume of the media within the reactor so that optimal cell growth is maintained. Once the desired cell density and volume is achieved, the cells are transferred to a production bioreactor.

In a preferred embodiment, the inoculation bioreactor includes an "inoculation well" located at the base of the reactor chamber. This inoculation well is supplied with fermentation sensors (pH, dissolved oxygen, temperature, optical density, etc.) to assist in assuring optimal cultivation conditions. Most preferably, this inoculation well is adapted to include an impeller drive by a continuously stirred tank reactor (CSTR) liquid agitation device.

SPECIFIC EMBODIMENTS

Materials and Methods

This seed-train expansion method was initially developed for a recombinant baby hamster kidney (BHK) cell line and a chinese hamster ovary (CHO) cell line expressing human proteins. Cells used for this invention were taken from 12 L perfusion bioreactor containing 20×10⁶ cells/mL. The cells were cultivated and frozen in mammalian cell culture medium based on a commercially available DMEM/Ham's F12 formulation (1:1) manufactured by JRH (Lenexa, Kans.) or Life Technologies (Grand Island, N.Y.) and supplemented with iron, Pluronic F68 (BASF, Pardipanny, N.J.), recombinant human insulin (Humulin, Eli Lilly, Indianpolis, Ind.), and essentially free of other proteins. The freezing medium contained 7.5% dimethylsulfoxide (Sigma, St. Louis, Mo.) as a cryoprotectant.

The cryopreservation bags (Cryocyte™ 250 mL or 500 mL, Nexell Therapeutics Inc. Irvine, Calif.) used for storage contained 50–100 mL of cell suspension and were frozen in a −40° C. freezer (Revco, Asheville, N.C.) prior to transferring to a liquid $N_2$ freezer (Forma Scientific, OH). The cells were concentrated to approx. 40×10⁶ cells/mL in 50 mL, or to 20×10⁶ cells/mL in 100 mL to ensure an initial bioreactor cell density of 1 million cell/mL in 2 L volume. Cell densities of 0.5–1 10⁶ cells/mL are commonly used to initiate a new seed-train expansion process.

The BHK cells in the cryopreservation bag were thawed using a 37° C. water bath. The cell suspension was transferred to a centrifuge tube, diluted with fresh medium (1:1) and gently centrifuged at 1000–1200 rpm. The supernatant was discarded, the cell pellet resuspended in fresh medium and transferred to a sterile bottle to inoculate the "inoculation well" bioreactor. This wash step is used to remove most of the DMSO and is common practice in mammalian cell culture. Later, this DMSO washing step was eliminated and the cells were directly transferred into the bioreactor from the bag. (Elimination of the DMSO wash step allows operation and maintenance of a closed system, thereby reducing the opportunity for system contamination. See Example 2.)

The same technology was also used for recombinant CHO-cells.

Two different bioreactors were used. However, both of them had the common feature of being able to inoculate into a 2 L volume "inoculation well".

1. 5 L cultures were carried out in Applikon 7 L bioreactors (Schiedam, The Netherlands) equipped with a sintered stainless steel frit (Mott Metallurgical, Farmington, Conn.) for aeration. A cell separation device was used to retain cells within the vessel and to allow for operation in continuous perfusion mode. The reactor system is capable of supporting at least 20 million cells/mL in 5 L volume. pH, dissolved oxygen, temperature, and optical density were measured via probes that were submerged in culture when a volume of at least 2 L was used. The reactor is designed with a 2 L volume stainless steel inoculation well.

Figure 1:
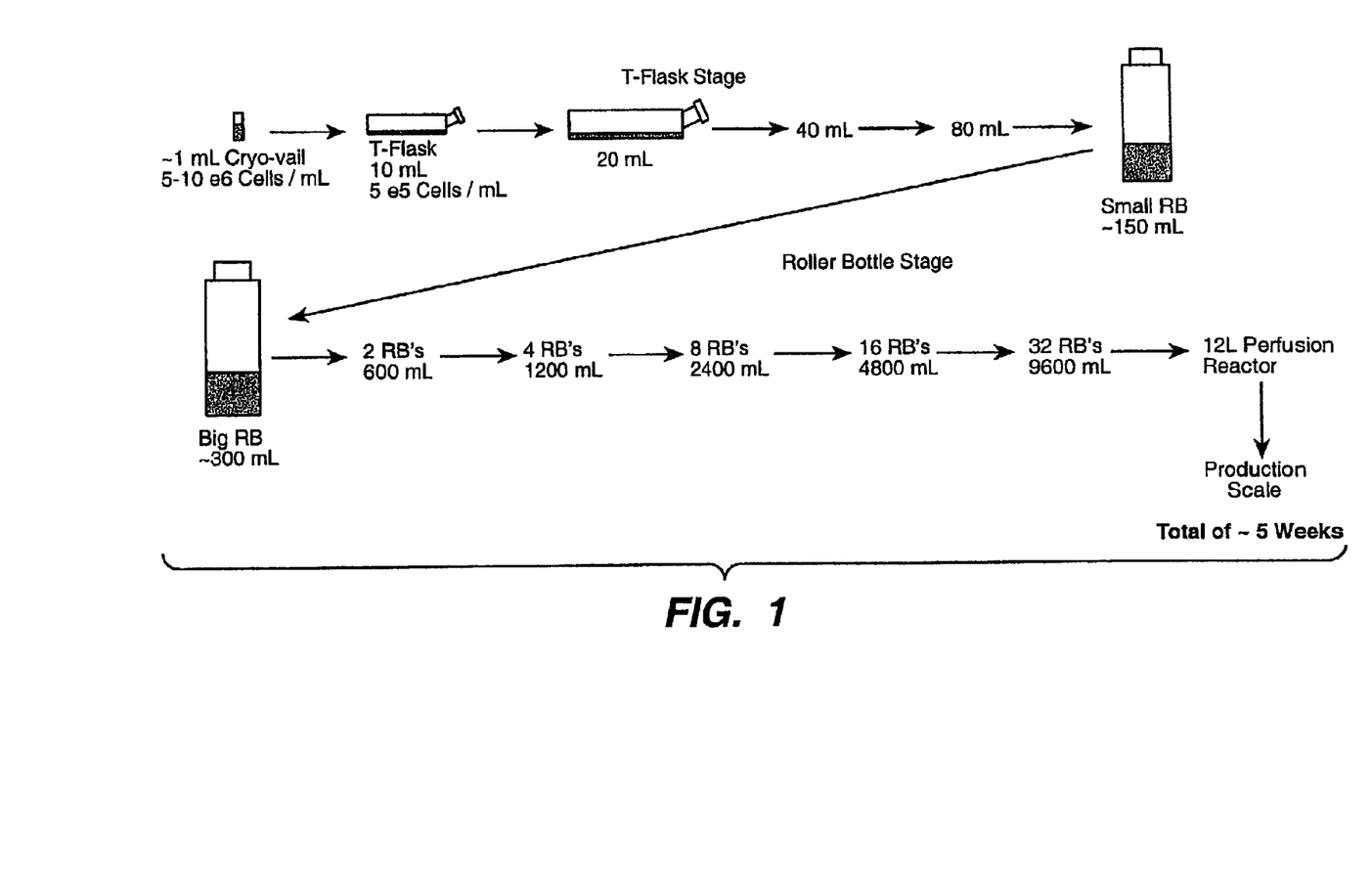
FIG. 1 illustrates the prior art of seed-train expansion method.
Figure 2:
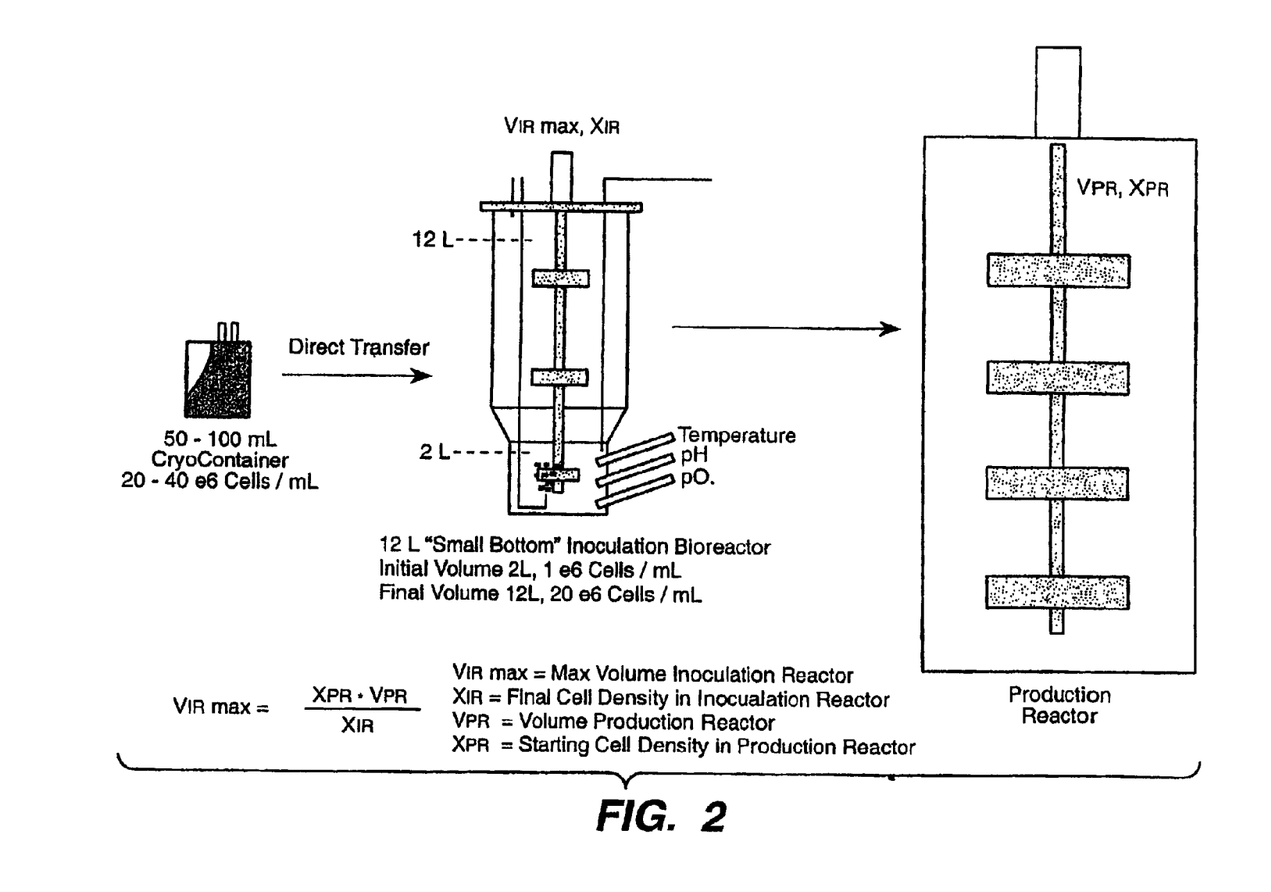
FIG. 2 shows the preferred method of this invention.
Figure 3:
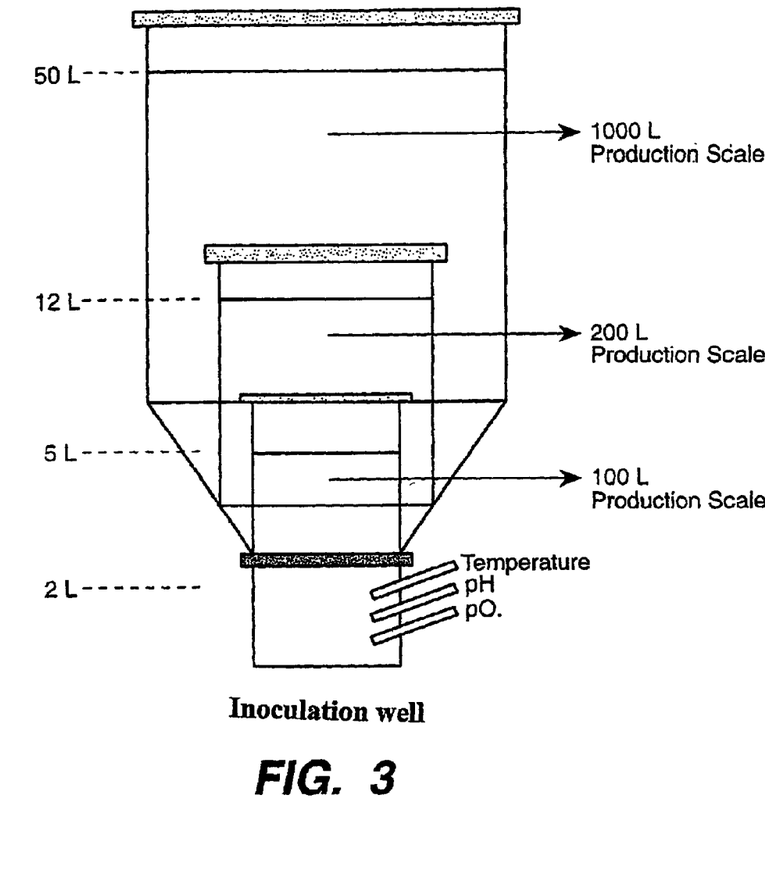
FIG. 3 shows the concept of the inoculation well inoculation bioreactor.

2. 12 L cultures were carried out in custom designed 15 L bioreactor. The stainless steel inoculation well of the reactor was the same (2 L volume) as in the 7 L vessel. However, a conical flange was used to extend the diameter and the volume of the top part (FIG. 3). Aeration was provided through a sintered stainless steel frit (Mott Metallurgical, Farmington, Conn.). A cell separation device was used for continuous perfusion technology. This reactor system is capable of supporting at least 20 million cells/mL in a 12 L working volume.

Both bioreactor systems were controlled using a B. Braun DCU (Digital Control Unit, B. Braun International, Melsungen, Germany) under operating conditions as reported elsewhere.

The relationship between the size and cell density of the used cryo-container and the inoculation well ($V_{IR\ min}$) of the inoculation reactor can be determined by following formula:

$$V_{IR\ min} = \frac{X_{bag} * V_{bag}}{X_{IR\ start}}$$

were $X_{bag}$ is the cell density in the cryo-container and $V_{bag}$ the volume. $X_{IR\ start}$ is the desired starting cell density in the inoculation well of the inoculation reactor, usually 1×10⁶ cells/mL.

The final volume of the inoculation reactor ($V_{IR\ max}$) depends on the volume of the production reactor that will be used and can be determined by the formula:

$$V_{IR\ max} = \frac{X_{PR} * V_{PR}}{X_{IR}}$$

where $X_{PR}$ is the targeted initial cell density in the production bioreactor (usually 1 10⁶ cells/mL), $V_{PR}$ the volume of the production reactor, and $X_{IR}$ the final cell density in the inoculum bioreactor. The inoculation well of the bioreactor will normally be small (in the present examples a 2L inoculation well was used) and the volume may be increased by increasing the diameter and the height of the bioreactor. Since $V_{IR\ max}$ is not limiting, the same "inoculation well" concept can be applied to the design of larger bioreactors. (see FIG. 3).

The cultures carried out in the 7 and 12 L systems had an initial volume of 2 L. This is the minimum volume necessary to submerge the bioreactor's pH, dissolved oxygen electrodes, as well as the temperature sensor. Aeration is carried out using headspace aeration just after inoculation. The volume is increased stepwise to keep the cell density between 0.8 and 1.2×10⁶ cells/mL. Oxygenation via gas sparging is used once the volume reaches four liters. The cell-specific perfusion rate was maintained at 0.5–0.7 nL/cell/day at all times.

Off-line sampling was performed daily to determine cell and metabolite concentrations. Cell counts and viability were determined using a hemacytometer and the trypan blue exclusion method. A YSI analyzer (Yellow Springs Instruments) was used to measure glucose, lactate, glutamate and glutamine concentrations of samples. LDH and ammonia were measured using a Kodak Biolyzer (Kodak Instruments, N.Y.). A NOVA blood gas analyzer (Nova Biomedical, Waltham, Mass.) was used to measure the dissolved $CO_2$ level and to check pH and dissolved oxygen values. Samples were analyzed for rFVIII activity by the one stage coagulation method. The product quality was determined by an in-house developed Western Blot assay.

EXAMPLE 1

Figure 4:
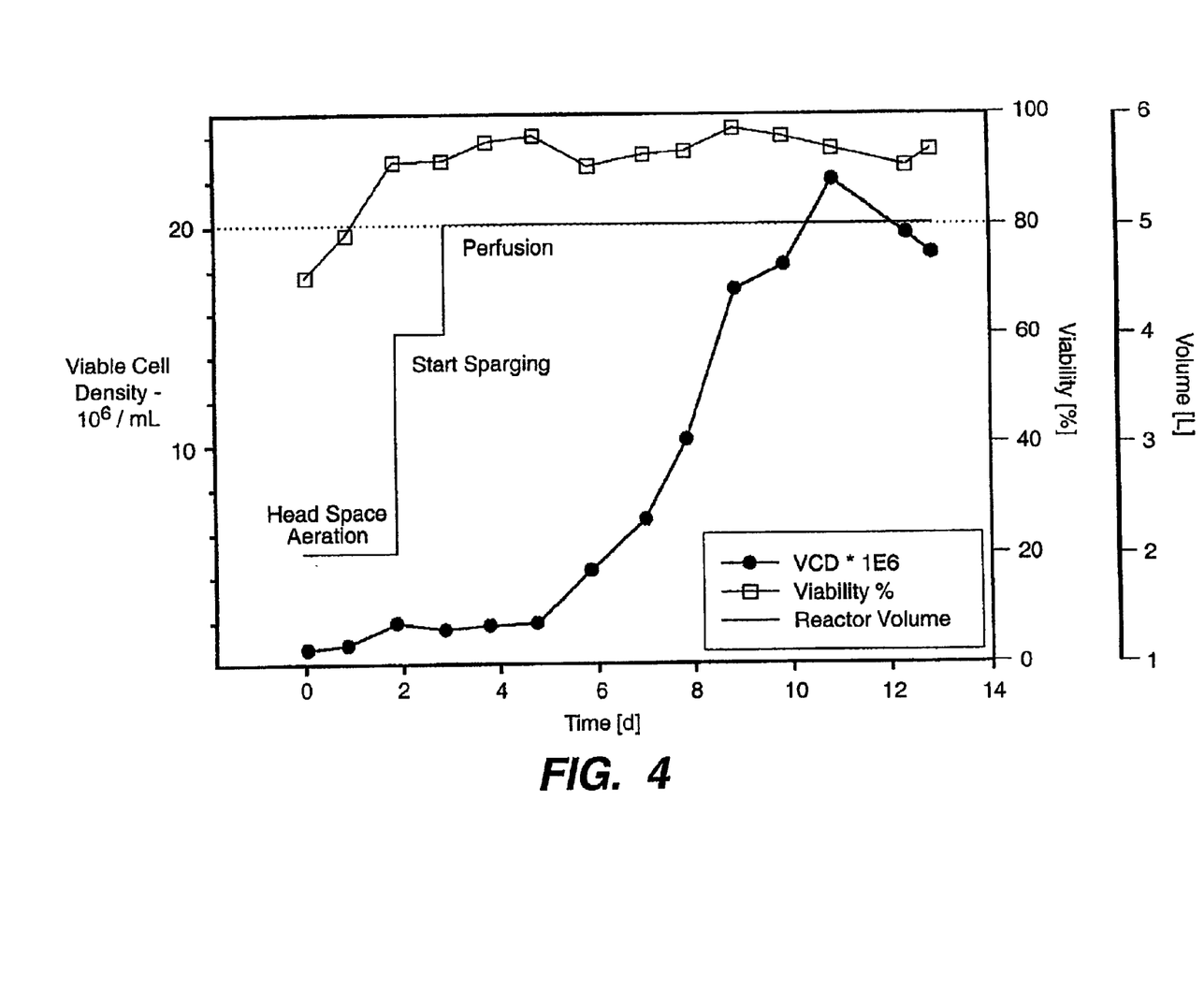
FIG. 4 shows a continuous perfusion culture performed in the 5 L "inoculation well" containing bioreactor, started with BHK cells cryopreserved in the 50 mL bag. The viable cell density (VCD [•]) and the viability profile [ ] are shown. Cell viability remained high throughout the culture. The target cell density of 20 million cells/mL at 5 L scale was reached within 12 days.

FIG. 4 shows a 12 L perfusion culture. 50 mL of cell suspension cryopreseved in an EVA bag was used for inoculation. The cells were washed with fresh medium to remove the DMSO before inoculation. The culture was at an initial volume of 2 L with headspace aeration. The cell viability exceeded 95% throughout the process and the volume was increased stepwise based on cell density. Gas sparging was used once the volume was at 4 L. Continuous medium perfusion was started one day after the volume reached 12 L. The perfusion rate was kept at 0.5–0.7 nL/cell/day. The target cell density of 20 $10^6$ cells/mL was reached after 11 days. The seed-train expansion experiment clearly demonstrates the elegance of this new expansion technology. No intermediate cell culture flasks were used, the risk of possible contamination was dramatically reduced, the media and environment were externally controlled, and as a result the time to start a production bioreactor was reduced by at least 70%.

EXAMPLE 2

A necessity of the DMSO removal step (wash/dilution) before the inoculation was evaluated. In this evaluation, two reactors were started in parallel from the same 50 mL bag freeze lot.

12 L reactor where a DMSO washing step was performed.

5 L reactor where a DMSO wash was omitted.

Figure 5:
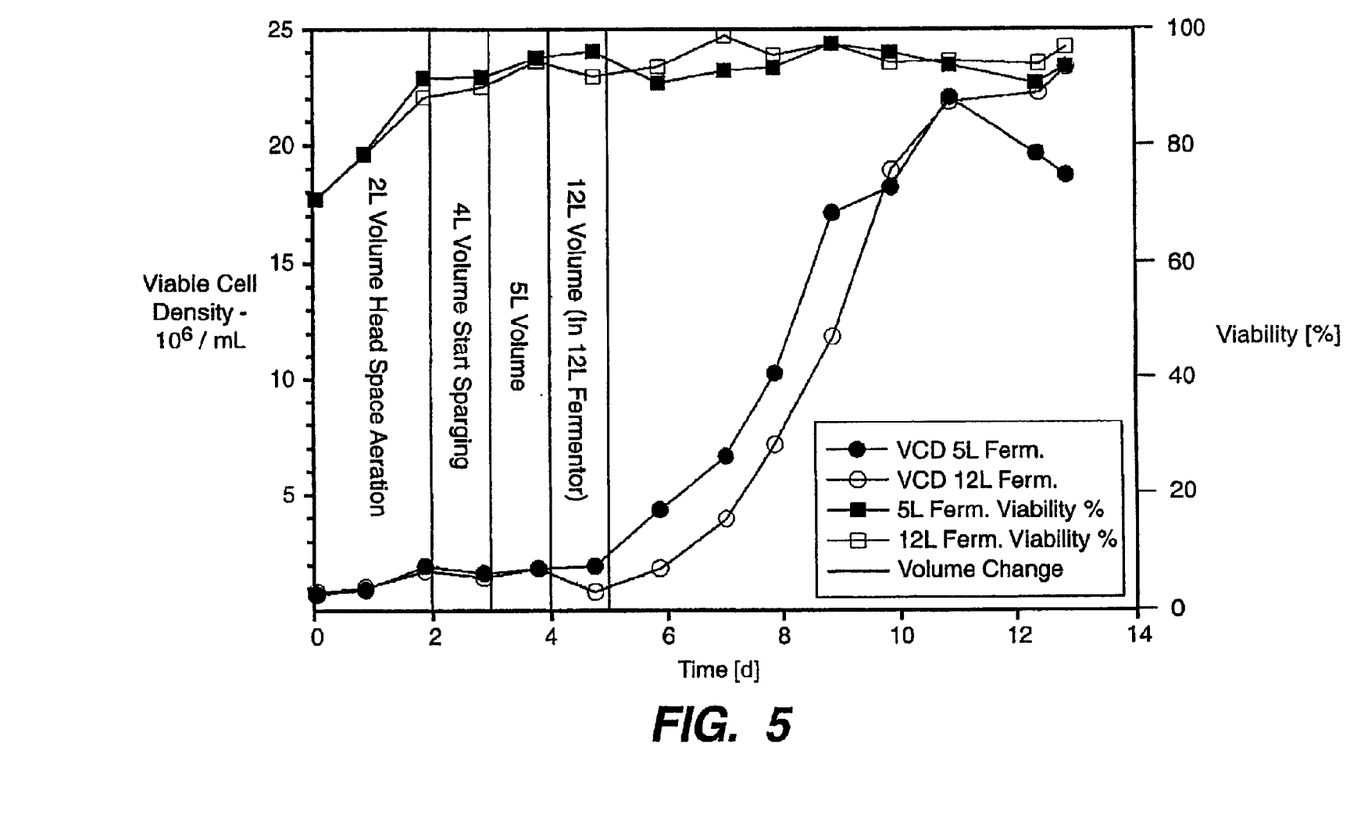
FIG. 5 illustrates the influence of a DMSO washing step during the seed-train expansion of BHK cells. In the 12 L culture (open symbols) a DMSO washing step was performed were as the second 5 L culture (filled symbols) was directly inoculated without washing the cells. As indicated no negative effect was observed, cell viability as well as cell growth showed no difference

Both cultures were run under the same conditions (volume increase steps, headspace aeration and sparging rates etc.). The 5 L culture reached the target cell density of 20 $10^6$ cells/mL within 11 days, the 12 L culture one day later. FIG. 5 shows a comparison of these two cultures. No difference in cell growth or viability was noticed. Elimination of the DMSO wash step further streamlines the seed-train expansion process (from cell thaw onwards) and allows for system closure throughout.

EXAMPLE 3

Figure 6:
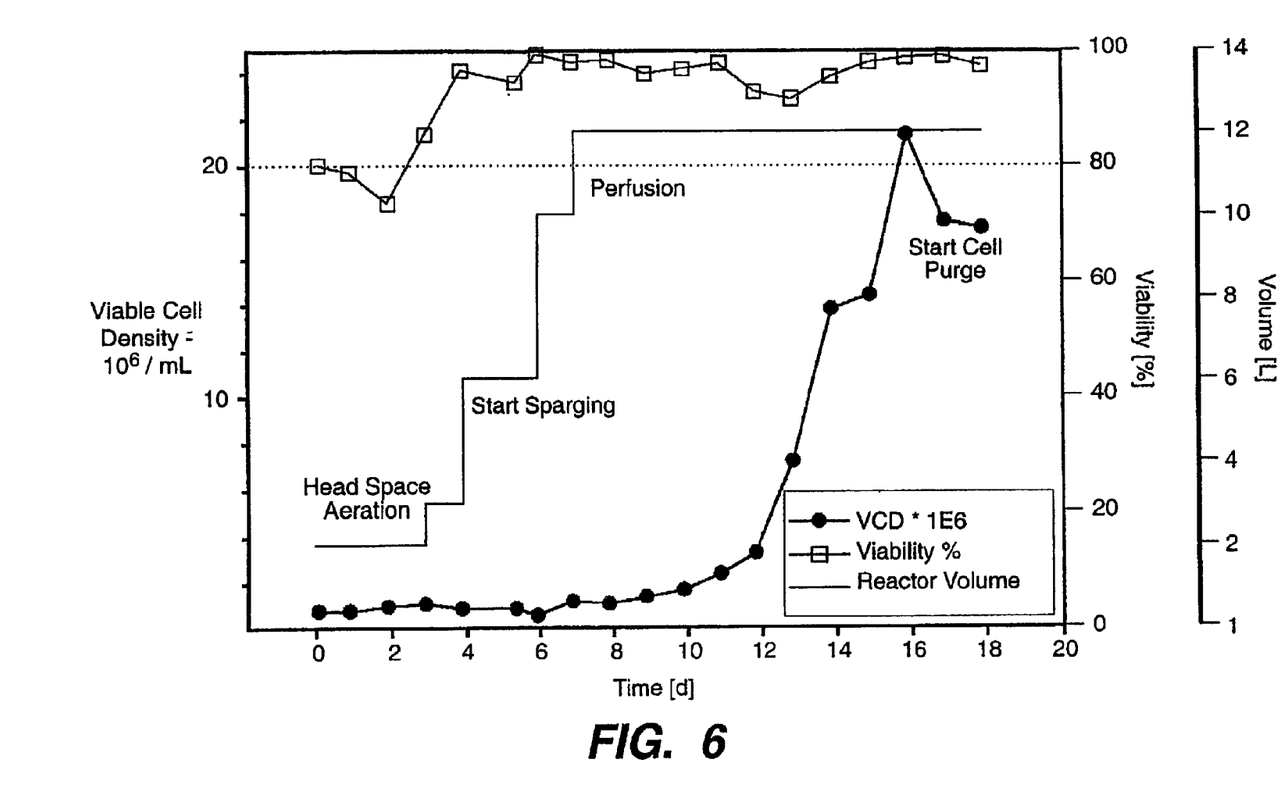
FIG. 6 shows a continuous 12 L bioreactor culture, started with BHK cells cryopreserved in the 50 mL bag, no DMSO wash was performed before the inoculation. The viable cell density (VCD [•]) and the viability profile [ ] are shown. The target cell density of 20 million cells/mL at 12 L scale was reached within 14 days.

FIG. 6 shows the time profile of a culture performed in the 12 L "inoculation well" reactor. 50 mL of cell suspension, cryopreseved in a bag, was used for inoculation without a DMSO wash. The target cell density of $20 \times 10^6$ cells/mL was reached after 16 days.

EXAMPLE 4

Figure 7:
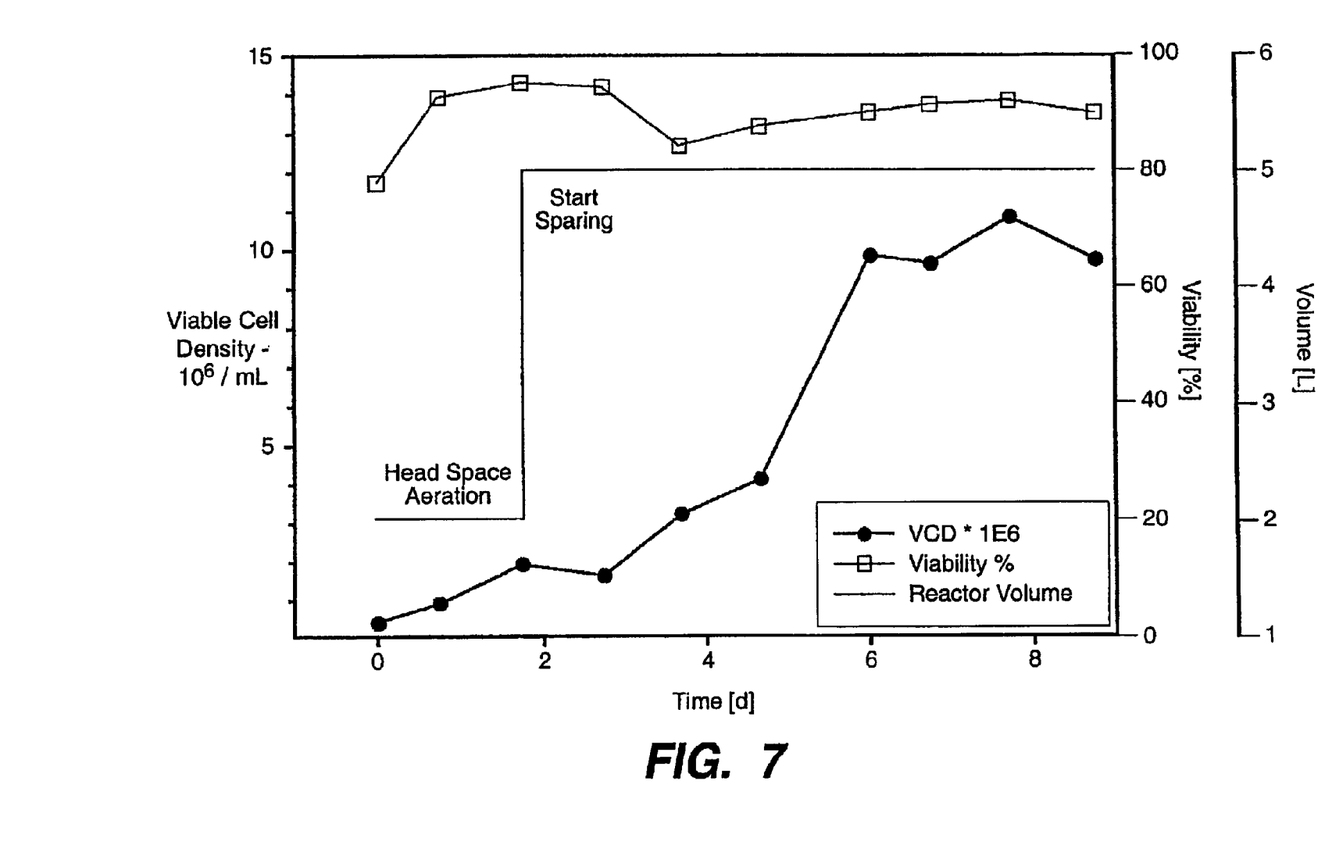
FIG. 7 illustrates a 5 L culture of recombinant CHO cells, started with CHO cells cryopreserved in a 50 mL bag, no DMSO wash was performed before the inoculation. The viable cell density (VCD [•]) and the viability profile [ ] are shown. The target cell density was reached within 6 days.

FIG. 7 shows the time profile of a CHO culture performed in the 5 L bioreactor. 50 mL of cryopreseved cells in a bag was used for inoculation. No DMSO washing step was performed. The target cell density—here $10 \times 10^6$ cells/mL were reached within 6 days.

EXAMPLE 5

Figure 8A:
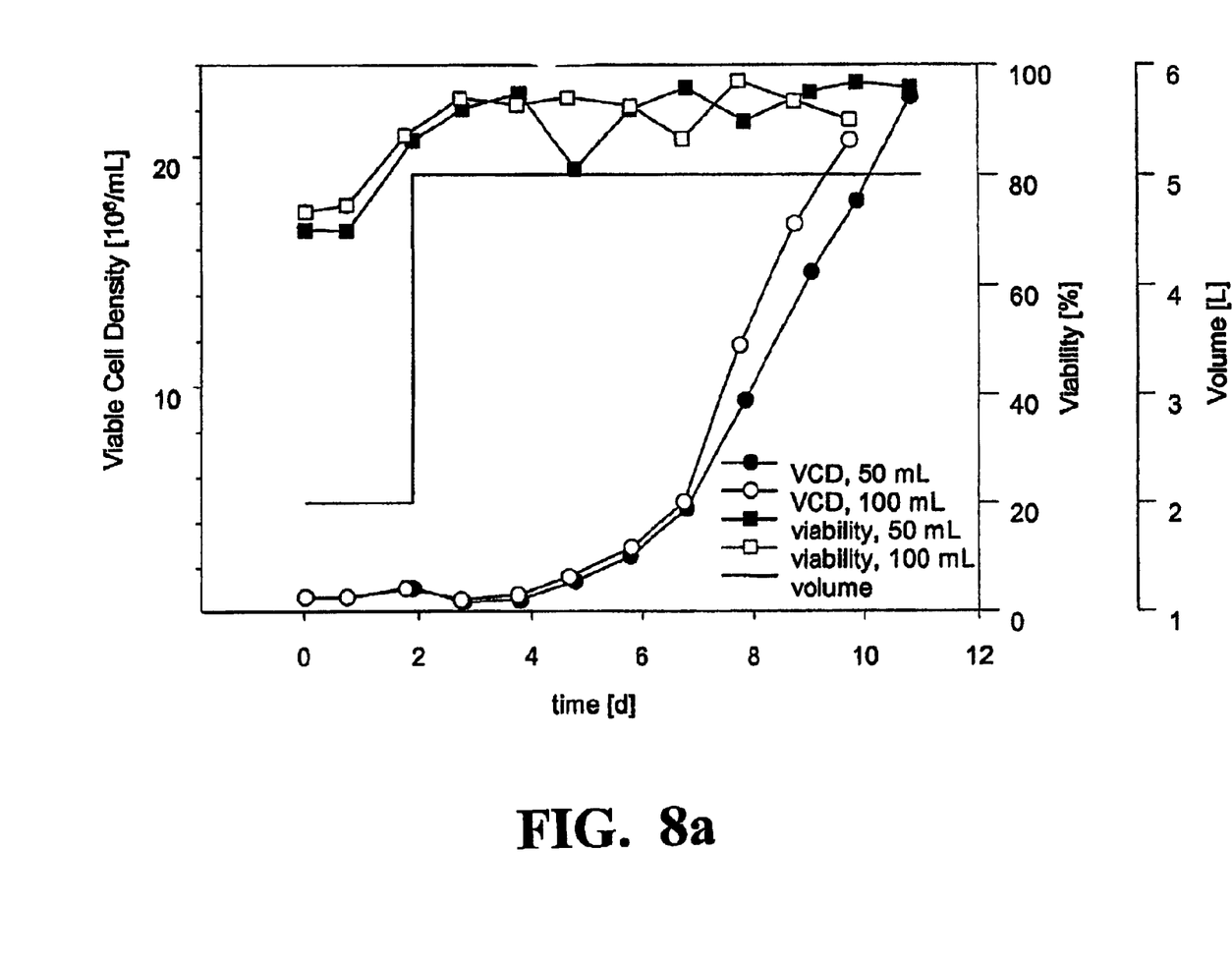
FIG. 8a illustrates two 5 L cultures started with rBHK cells cryopreserved in a 50 mL bag, a second culture in a 100 mL bag, no DMSO wash was performed before the inoculation. The viable cell density (VCD [•]) and the viability profile [ ] are shown. The target cell densities of 20 million cells/mL at 5 L scale was reached within 10 days in both cultures.
Figure 8B:
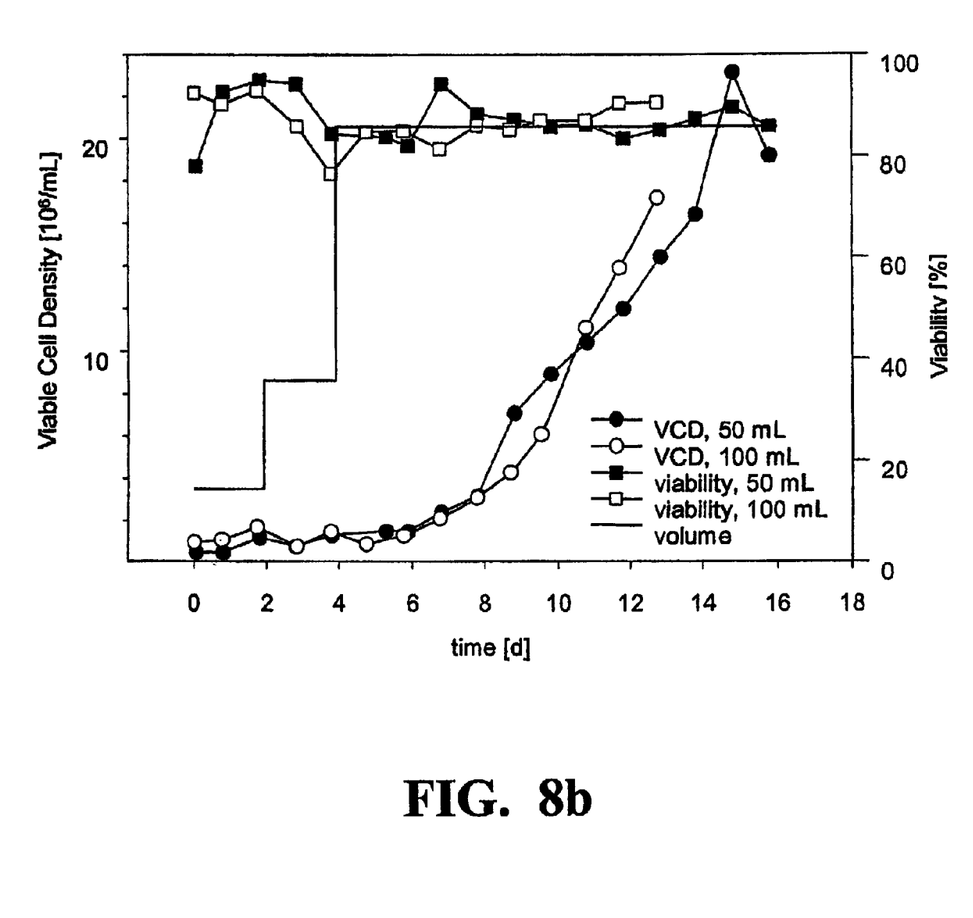
FIG. 8b illustrates two 12 L cultures started with recombinant CHO cells cryopreserved in 50 mL and 100 mL bags, no DMSO wash was performed before the inoculation. The viable cell density (VCD [•]) and the viability profile [ ] are shown. No negative effect was noticed in both cultures.

FIGS. 8a and 8b show the time profiles of two BHK and two CHO cultures performed in the inoculation bioteactors. 50 and 100 mL cryobags were used for inoculation, no DMSO washing step was performed in all four cultures. No negative effect was noticed using either 50 mL or 100 mL cryobags.

SUMMARY

In general, existing seed-train expansion methods for mammalian cell culture are labor intensive and susceptible to microbial contamination due to the use of multiple cultivation vessels such as T-flasks, roller-bottles and spinner flasks. A new seed-train expansion method was developed utilizing 50 mL or 100 mL EVA cryopreservation bags that are used to inoculate directly into a custom built "inoculation well" in a bioreactor. This reactor serves as the inoculation source for a production scale system. This methodology completely eliminates the use of any T-flasks, roller bottles or spinner flasks during the scale-up. A procedure for sizing and design of the "inoculation well" reactor is proposed. Following this procedure, the method can be applied for the direct inoculation of any scale production reactor. Cryopreserved cells were used in these examples, but cryopreservation is not a requirement of this technology. Mammalian cells at standard temperatures can be substituted for the cryopreserved cells and the effectiveness and utility of the system would remain the same. Similarly, the size of the bioreactor can be adjusted, so that as long as the concepts of an inoculation well and the method of use are maintained.

The Examples presented above are provided to illustrate one organization design for the invention. Accordingly, it is intended that the scope of this invention should be limited only by the claims below.

We claim:

1. In an inoculation bioreactor, a method of mammalian cell seed-train expansion comprising:
   a) providing an inoculation bioreactor having an inoculation well,
   b) adding mammalian cell culture media to said inoculation well,
   c) delivering a cryopreservation bag quantity of mammalian cells to the media within the inoculation well,
   d) controlling environmental conditions and composition of said media so that cell growth within the inoculation well is optimized and desired cell density achieved, and
   e) increasing the media volume incrementally while maintain optimum environmental conditions and environmental growth conditions until the inoculation bioreactor is filled to a predetermined volume and cell density.

2. The method of claim 1, wherein the mammalian cells are selected from the group consisting of Chinese hamster ovary cells and baby hamster kidney cells.

3. The method of claim 1, wherein the inoculation bioreactor has a volumetric capacity of about 7 Liters.

4. The method of claim 1, wherein the inoculation bioreactor has a volumetric capacity of about 15 Liters.

5. The method of claim 1, wherein the inoculation well has a volumetric capacity of about 2 Liters.

6. The method of claim 1, wherein the cryopreservation bag quantity of mammalian cells has a volume of between about 50 and 100 milliliters, and the cell density is between about $20 \times 10^6$ cells per milliliter and $40 \times 10^6$ cells per milliliter.

* * * * *